United States Patent
Dinges et al.

(10) Patent No.: US 8,135,957 B2
(45) Date of Patent: Mar. 13, 2012

(54) ACCESS CONTROL SYSTEM BASED ON BRAIN PATTERNS

(75) Inventors: Clemens Dinges, Obermichelbach (DE); Michael Schlereth, Wilhermsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 773 days.

(21) Appl. No.: 11/895,234

(22) Filed: Aug. 23, 2007

(65) Prior Publication Data

US 2008/0229408 A1    Sep. 18, 2008

(30) Foreign Application Priority Data

Aug. 23, 2006 (EP) .................................... 06017535

(51) Int. Cl.
*G06F 21/00* (2006.01)
*G06K 9/00* (2006.01)
*A61B 5/04* (2006.01)

(52) U.S. Cl. .......................... 713/186; 382/115; 600/544
(58) Field of Classification Search .................. 713/186; 382/115; 600/544
See application file for complete search history.

(56) References Cited

U.S. PATENT DOCUMENTS

| | | | |
|---|---|---|---|
| 4,987,903 A | 1/1991 | Keppel et al. | |
| 5,325,862 A * | 7/1994 | Lewis et al. | 600/544 |
| 5,816,247 A * | 10/1998 | Maynard | 600/544 |
| 6,011,991 A * | 1/2000 | Mardirossian | 600/544 |
| 6,160,903 A * | 12/2000 | Hamid et al. | 382/115 |
| 6,293,904 B1 * | 9/2001 | Blazey et al. | 600/26 |
| 6,349,231 B1 | 2/2002 | Musha | |
| 6,434,259 B1 * | 8/2002 | Hamid et al. | 382/115 |
| 7,542,590 B1 * | 6/2009 | Robinson et al. | 382/115 |
| 7,543,155 B1 * | 6/2009 | Kobylak et al. | 713/184 |
| 7,594,122 B2 * | 9/2009 | Milgramm et al. | 713/186 |
| 7,689,833 B2 * | 3/2010 | Lange | 713/186 |
| 2002/0154793 A1 * | 10/2002 | Hillhouse et al. | 382/115 |
| 2005/0022034 A1 * | 1/2005 | Chaudhari et al. | 713/202 |
| 2007/0110283 A1 * | 5/2007 | Hillhouse et al. | 382/115 |

(Continued)

FOREIGN PATENT DOCUMENTS

| | | |
|---|---|---|
| DE | 102 31 870 A1 | 1/2003 |
| DE | 103 29 901 A1 | 1/2005 |
| GB | 2 314 436 A | 12/1997 |
| WO | WO 03/093947 A2 | 11/2003 |

OTHER PUBLICATIONS

M. Poulos et al.: "Person identification based on parametric processing of the EEG", Electronics, Circuits and Systems, 1999. Proceedings of ICECS '99. The 6th IEEE International Conference on Pafos, Cyprus, Sep. 5-8, 1999, Piscataway, NJ, USA, IEEE, US, vol. 1, Sep. 5, 1999, pp. 283-286, XP 010361548.

(Continued)

*Primary Examiner* — Christian Laforgia

(57) ABSTRACT

The invention includes a control system and a method for access control of an application system, with electrically measurable data acquired as the result of a biometric reaction of a user, the biometric reaction triggered by stimulatory information presented to the user. An acquisition means for acquiring the electrically measurable data, a provision means for providing reference data and a comparison means for comparing the data are provided in the control system. The reference data is provided relating to the stimulatory information and/or the acquired, electrically measurable data. The acquired measurable data is compared with the provided reference data by means of the comparison means. An authorization of the user to the application system takes place on the basis of the comparison results. By means of this control system it is possible to dynamically authorize and identify a user with absolute reliability and to unambiguously authenticate said user.

10 Claims, 3 Drawing Sheets

U.S. PATENT DOCUMENTS

2008/0005578 A1* 1/2008 Shafir .................... 713/186
2008/0294907 A1* 11/2008 Hively .................... 713/186
2009/0063866 A1* 3/2009 Navratil et al. .......... 713/186

OTHER PUBLICATIONS

M. Poulos et al.: "Neural network based person identification using EEG features", Acoustics, Speech, and Signal Processing, 1999. Proceedings, 1999 IEEE International Conference on Phoenix, AZ, USA, Mar. 15-19, 1999, Piscataway, NJ, USA, IEEE, US, vol. 2, Mar. 15, 1999, pp. 1117-1120, XP010328414.

R. B. Paranjape et al.: "The electroencephalogram as a biometric", Electrical and Computer Engineering, 2001, Canadian Conference on May 13-16, 2001, Piscataway, NJ, USA, IEEE, vol. 2, May 13, 2001, pp. 1363-1366, XP010551031.

* cited by examiner

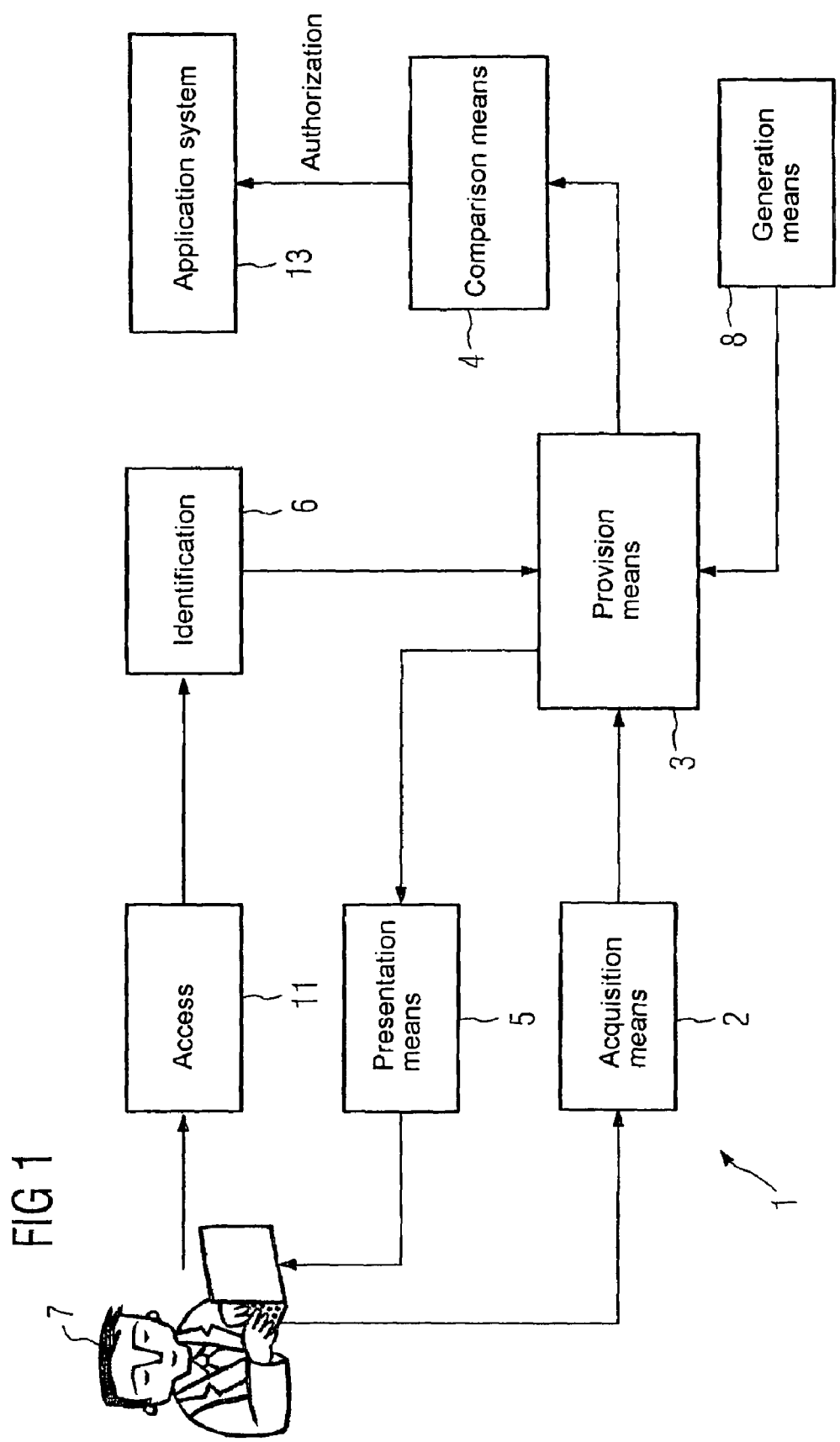

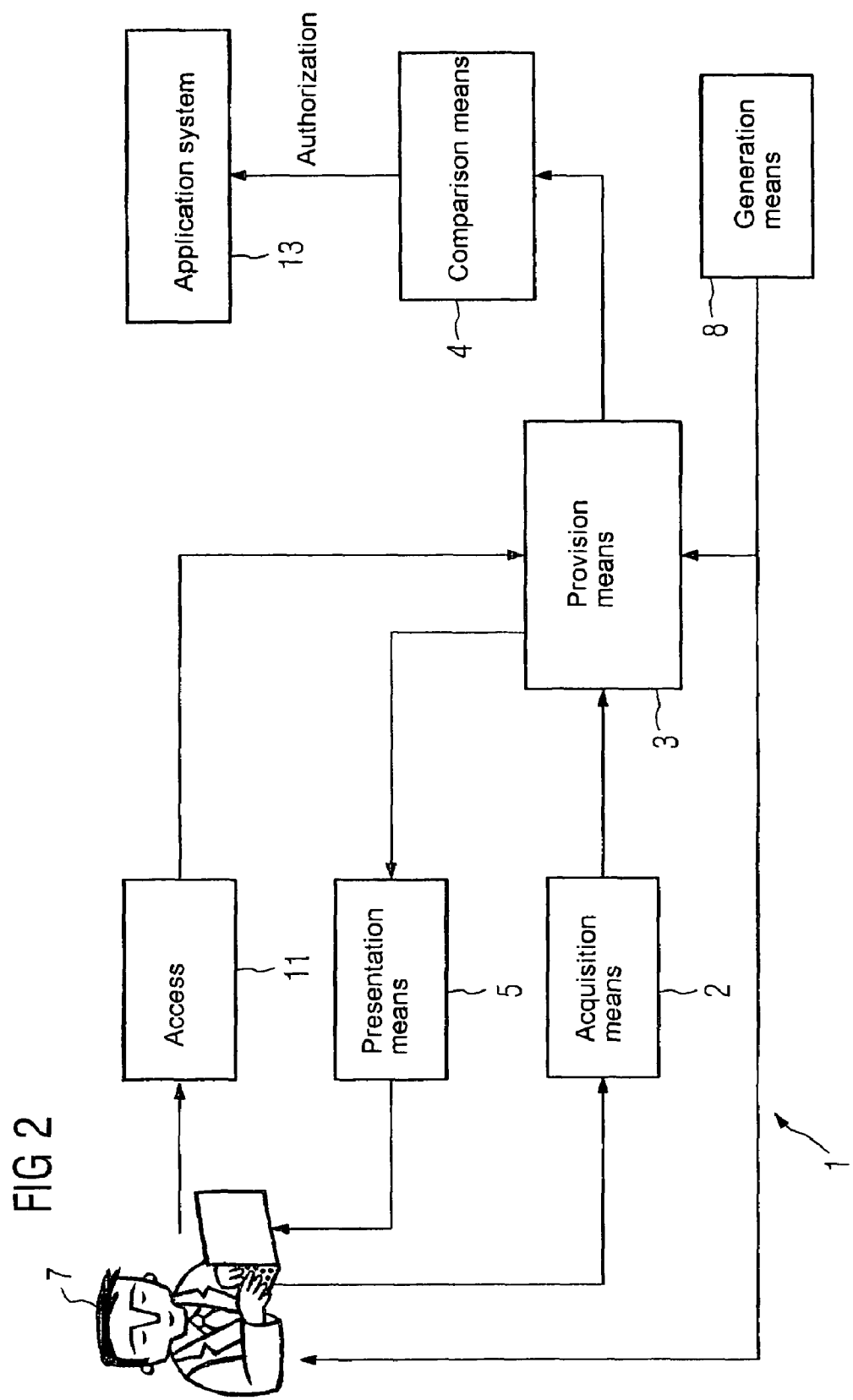

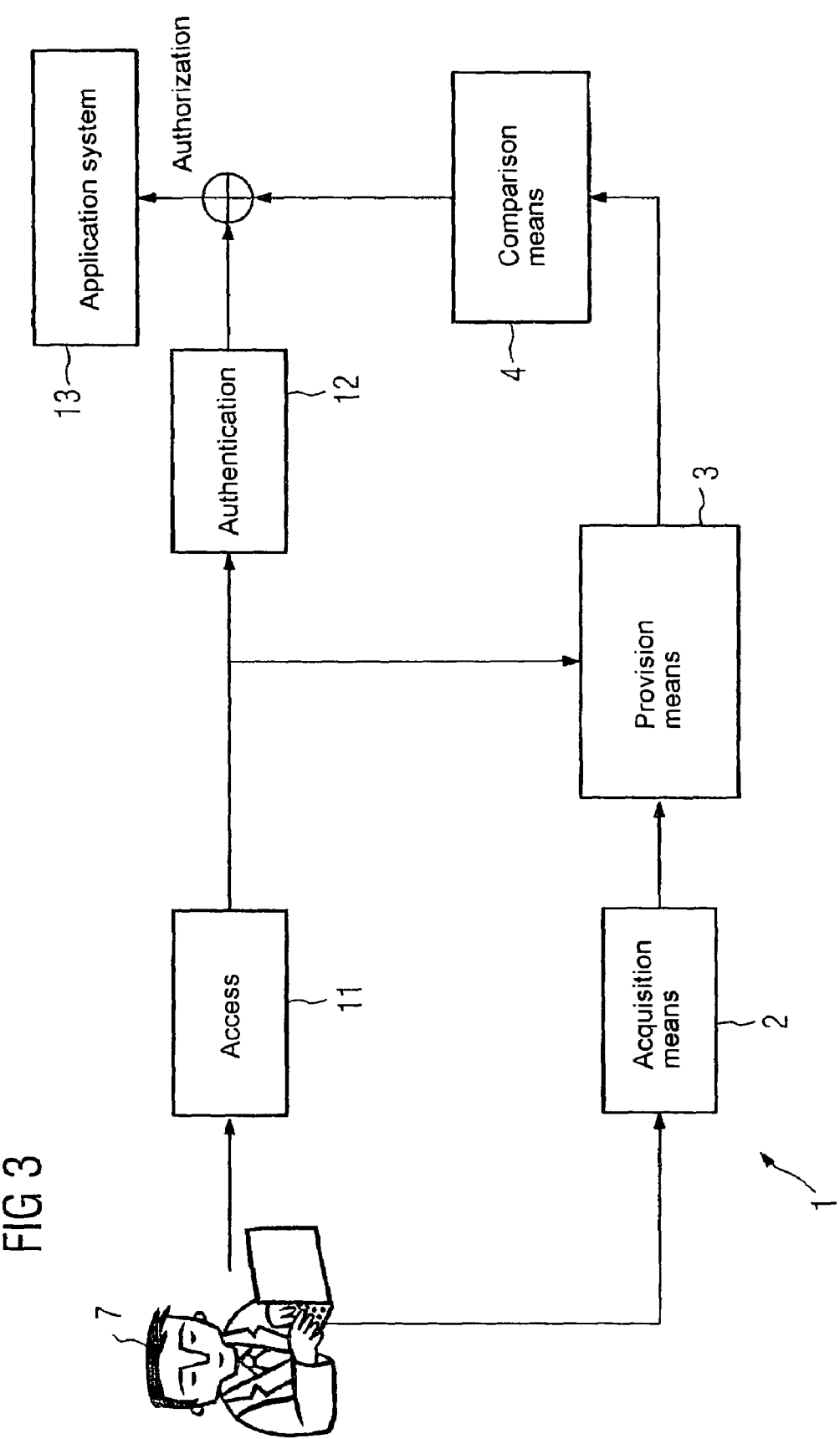

ACCESS CONTROL SYSTEM BASED ON BRAIN PATTERNS

CROSS REFERENCE TO RELATED APPLICATIONS

This application claims priority of European application No. 06017535.3 filed Aug. 23, 2006, which is incorporated by reference herein in its entirety.

FIELD OF INVENTION

The invention relates to a system for access control with an acquisition means for acquiring electrically measurable data resulting from a biometric reaction of a user and a method for access control based on a biometric reaction of a user.

BACKGROUND OF THE INVENTION

To uniquely identify, authenticate and authorize a person in order to just grant the person the rights assigned to him, for example with respect to the operation of a system or access to a system, is at present becoming increasingly important. The conventional access control systems have long since reached their limits with respect to these increased requirements. Furthermore, the authentication of a user is based on hardware components (codes, chip cards etc.) or on password systems (password, PIN/TAN etc.). They can be relatively easily overcome using criminal methods such as the kidnapping or blackmail of the key holder, robbery or duplication of chip cards, data theft etc, and can possibly be lost or forgotten. For these reasons, such access control systems cannot meet the increased security requirements.

In addition to the authentication, the administration of the authorization plays an ever more important role due to the increasingly frequent changeover of administrative personnel, even though administration is very expensive. Up to now, the authorization of persons for a specific application was usually carried out by an empowered person (e.g. the system administrator) who granted authorizations. The granting of an authorization often takes a long time because administration and approval procedures must be complied with. Where there are changes in tasks, the granted authorization has to be reassigned if necessary.

Newer, more efficient approaches, based on biometric methods for example, can also often not really be applied in the harsh working environment of the production process because they usually require a clean, office-type working situation for the optical or electrical detection process. Furthermore, the biometric methods used so far have an unacceptable failure rate, especially if only a biometric method is used for access control.

SUMMARY OF INVENTION

The object of the invention is to increase accuracy during access control. This object is achieved according to the invention by a control system with the features of the claims and by a method with the features of the claims. The dependent claims relate to advantageous developments and embodiments of the system or method.

The invention is based on the idea that the mental activity of a person is accompanied by a biometric reaction, especially their brain waves, with the biometric reaction being distinctly different with each person. Accordingly, a control system for controlling access to an application system is provided, comprising an acquisition means for acquiring electrically measurable data of a user, a provision mean for providing reference data and a comparison means for comparing data. The electrically measurable data is the data generated as a result of a biometric reaction of the user, with this biometric reaction being triggered by stimulatory information presented to the user. The reference data relating to the stimulatory information and/or the acquired electrically measurable data is provided by the provision means. This also allows reference data to be provided which is either specific to the person or unrelated to the person. The acquired data is compared with the provided reference data by means of the comparison means. An authorization of the user with respect to the application system takes place on the basis of the comparison results. The control system according to the invention allows a new dynamic authorization scheme, namely a so-called "ad hoc" authorization. The granting of a right of access to the application system then only takes place at the time instant of the authorization request and depends on the status of the user. In other words, the authorization can take place not only specifically to the person but also with respect to qualifications, with it being possible for the qualifications to refer, for example, either to the current mental state of the user, such as fatigue, or to existing know-how, i.e. the operational capability of the user. In this way it is possible to identify a user with absolute reliability and to unambiguously authenticate the same. Furthermore, the unmistakable biometric identification is used in security checking or identification, with it being possible to use evoked electrical potential, such as EEG signals (electroencephalogram) for accurate, unavoidable identification and authentication, including authorization.

According to an advantageous embodiment of the invention, the control system has a means for representing the stimulatory information so that the stimulatory information can be presented to the user. The stimulatory information can, for example, be an optical pattern (e.g. pictogram, image, video sequence) or an acoustic signal such as noise, speech, sound sequence or music sequence.

Furthermore, a group of patterns (pattern sets) can also be used in combination as stimulatory information. By the presentation of the pattern sets, the users of the relevant groups can, for example, be distinguished in such a way that the users can be partly made known or not made known with the pattern sets. This "coding", which makes the user partly known or unknown with the pattern sets, allows the number of different patterns, or the probability of a false identification, to be reduced. If, for example, ten patterns are used and of these seven are presented to the user this enables 120 users to be coded.

Advantageously, the stimulatory information is assigned to either a designation or identification of the user. The user can enter his designation or identification by means of the control system. In this way, the stimulatory information can be presented and assigned as a function of the individual user.

Advantageously, the reference data is replaced by the current, acquired electrically measurable data. Furthermore, repeated application of the stimulatory information can be adjusted so that the repeated presentation of a stimulus changes the mental, and therefore the biometric reaction, e.g. the EEG signal, of the user.

By means of the control system, a user can also be authorized only on the basis of his recollection of the stimulatory information. In this case, the stimulatory information is not used to authenticate the identification of the user, but instead a unique authorization is assigned to the stimulatory information itself. The stimulatory information is presented, before the access control, exclusively to the user who is to be authorized for the application system. This stimulatory information is not used again after its comparison with the corresponding reference data.

According to a further advantageous embodiment of the invention, the electrically measurable data is acquired on the basis of a mental state of the user. The stimulatory information in this case can occur by means of the environmental situation. In this way, the control system determines what mental state or current physical and psychical condition triggers this situation with the user, and what know-how he possesses. The authorization of a user can therefore take place dynamically. A user is then authorized only if, for example, he has the necessary know-how and can manage the system in a certain situation.

Advantageously, the biometric reaction is measured by an EEG (electroencephalogram), EOG (electrooculogram) or EMG (electromyogram). Such methods enable the evoked electrical potential to be measured as unchangeable characteristics of humans. For example, whether or not the stimulus is known to the user can be determined by an EEG reading.

According to the control system presented above, a method for controlling access to an application system is provided, in order to reliably recognize and definitely authenticate a user. By means of this method, electrically measurable data is acquired on the basis of a biometric reaction of the user, with the biometric reaction being triggered by stimulatory information presented to the user. Reference data relating to the stimulatory information and/or the acquired, electrically measurable data is provided. The acquired measurable data is compared with the provided reference data and an authorization of the user with respect to the application system takes place on the basis of the comparison results.

BRIEF DESCRIPTION OF THE DRAWINGS

The invention is described and explained in more detail below with the aid of the exemplary embodiments shown in the figures, in which;

FIG. 1 shows an inventive access control based on person-related recordings.

FIG. 2 shows an inventive access control for an anonymous authorization.

FIG. 3 shows an inventive access control based on situation-specific mental states.

DETAILED DESCRIPTION OF INVENTION

FIG. 1 shows a brain pattern-based access control of an application system 13 according to a control system 1, with the authentication taking place on the basis of a person-related recording. In control system 1, an acquisition means 2 for acquiring electrically measurable data of a user 7, a provision means 3 for providing reference data and a comparison means 4 for data comparison are provided. The electrically measurable data is generated on the basis of a biometric reaction of the user 7, with this biometric reaction being triggered by stimulatory information presented to the user 7. The biometric reaction is the brain reaction of the user 7 and is measured by an EEG. Furthermore, a presentation means 5 for generating the stimulus and a generating means 8 for generating the stimulus in the control system 1 are provided. The stimulus can also be a group of patterns (pattern sets).

The access control shown in FIG. 1 takes place in two steps, i.e. the conditioning and the authentication. An authorization assigned to the authentication is also possible. To provide the necessary reference data or identification 6 for a user 7 the conditioning is carried out before the authentication. User information of the user 7 is assigned by the provision means 3 to the generated stimulus for the identification 6. To condition the user, the generated stimulus is presented to the user via the presentation means 5. A biometric reaction, e.g. the electrical activity of the brain (brain pattern) triggered by the stimulus, or sometimes in combination with other biometric features, of the user 7 is measured by the acquisition means 2 and recorded as reference data and assigned to the user 7. The relevant reference data is provided by the provision means 3 on the basis of this stimulus or the acquired brain patterns. In this connection, the data of the identification 6 of the user 7 can be assigned to the reference data. It is also possible to assign a mental state (e.g. operational capability and fatigue, etc.) of the user 7 to the reference data. Generally, the reference data is stored in a database together with the identification data and a generated stimulus.

If after conditioning the user 7 wishes for example to access a protected area (application, space) via access 11 of the application system 13, he provides his identification 6 to the control system 1. The stimulus assigned to his identification 6 is then presented to him from the conditioning phase by the presentation means 5. By means of the comparison means 4, the control system 1 compares the data, acquired with respect to the brain pattern of the user 7, with the corresponding reference data that was acquired in the conditioning step, and checks whether the reaction lies within a certain tolerance range. The authorization of the user 7 can take place after the comparison result. If the comparison result is above a specified acceptance threshold, the control system 1 considers it suitable and accepts the user 7, otherwise the control system 1 considers it unsuitable and the user 7 is rejected. If the decision is positive, the acquired data is re-stored as reference data, so that in this way, in the event of repeated application, an adjustment can be made so that the repeated presentation of a stimulus changes the mental reaction.

FIG. 2 shows a different form of embodiment of the control system 1. This type of authorization is not necessarily person-related and also not limited to one person. As can be seen from FIG. 2, no user information is assigned to the generated stimulus because the user does not have to reveal his identification data (password, user name) to the control system 1. According to the example in FIG. 1, the access control also takes place in two steps, i.e. the conditioning and the authorization. The conditioning in this is anonymous conditioning, with the stimulus not being used to authenticate the user 7, but instead a unique authorization is assigned to the stimulus itself. If the stimulus has been presented to an unauthorized person, an authorized person then has no system access by means of this stimulus. Therefore the stimulus can, for example, only be presented to the user after he has made a special user request. Conditioning of this kind can also take place outside the control system 1, e.g. on a conventional computer via the internet. The stimulus can, for example, be sent to any person by post as a picture.

It is particularly useful if the authorized person himself wishes to prevent anybody other than himself from being able to use the authorization. It is very important to note that before the authorization the stimulus is presented only to the user 7 who is to be authorized. Therefore, the generation means 8 should be capable of generating such stimuli, with the stimuli having a high probability of not previously having been presented to a possible user and nevertheless having a high recognition value. This requirement can also be met by a combination of several similar or different stimuli.

If the user 7 wishes to access the application system 13 via access 11, the stimulus is presented with the access control. The biometric reactions of the user 7 can be triggered by a recollection of the presented stimulus. From the mental reaction of the user 7 it can be determined whether he has recognized the stimulus or not. If the stimulus is known to the user 7, he can be directly authorized. Because the presentation of the stimulus is independent of the individual user, the stimulus can be known to a person that is not to be authorized. Therefore the stimulus cannot be used again after the first attempt.

An important difference from the embodiment in FIG. 1 is that with the system in FIG. 1 the authenticity of the user is checked (to which an authorization is coupled) whereas in the system in FIG. 2 the stimulus can be assigned directly to the authorization of the user without the identity of the user being known (anonymous authorization). The embodiment shown in FIG. 2 can also be used to acquire the "security risk profiles" of all persons, which can be regularly acquired, for example by access controls at airports, high-rise buildings or other vulnerable locations. By means of an EEC reading it can be determined whether terms, scenes or other things are known to anybody.

In contrast to the aforementioned two embodiments, FIG. 3 shows an access control based on the situation-specific mental state of users. No conditioning is required in this case. The authorization takes place directly from the conditions of a user 7, with mental fitness or the degree of education of the user 7 being possible conditions. Therefore, the stimulus takes place through the environmental situation, e.g. a malfunction situation. The control system 1 assesses the mental state which this situation triggers in the user 7, e.g. confusion, self-assurance, certainty/uncertainty. Although the user 7 can be authenticated with access 11, he does not, however, automatically obtain all the assigned access rights after the successful authentication 12. A check is carried out to determine whether he is also mentally in a position to exercise these rights at the actual time instant and therefore to perform the task. Therefore the user 7 can be authorized on the basis of this assessment. Authorization thus takes place dynamically according to the know-how and current physical and psychical state of the user 7. An example of this would be that the user 7 has no right of access to a certain machine/system of the application system 13 even if he has already been authenticated/identified for the application system 13. If a fault occurs, the control system 1 can decide on the basis of the mental state of the user 7 whether he detects a malfunction situation and whether he has the knowledge sufficient for the task. According to the result of this decision, the user 7 can rectify the malfunction or call on a colleague for assistance.

In emergency, it is also possible that a person who can rectify the malfunction has, as a result of the decision, direct right of access to the application system 13 even if previously he was not acknowledged as the user of the application system 13. This scenario is, for example, particularly advantageous where external personnel are used for service tasks (servicing, cleaning etc.). Even if the password of the user 7 has been stolen by someone, the control system 1 can determine whether a person is actually the person that he claims to be.

The invention claimed is:

1. A control system for controlling access to an application system, comprising:
   a presentation device for presenting stimulatory information to a user, wherein the stimulatory information is presented exclusively to the user who is to be authorized for an application system, and wherein no user information is assigned to the stimulatory information;
   an acquisition device for acquiring current data comprising electrically measurable data as a result of a biometric reaction comprising a brain pattern of the user presented with the stimulatory information;
   a storage device that assigns a unique authorization to the stimulatory information;
   a comparison device that compares the acquired current data to provide a comparison result, wherein from a mental reaction of the user it is determined whether the user has recognized the stimulatory information,
   wherein the biometric reaction of the user is triggered by a recollection of the presented stimulatory information, and
   wherein, if the stimulatory information is known to the user, the user is directly authorized for the application system.

2. The control system as claimed in claim 1, further comprising a stimulatory information generating device that generates the stimulatory information.

3. The control system as claimed in claim 1, wherein the stimulatory information comprises one or more of an optical pattern, an acoustic pattern, or a combination thereof.

4. The control system as claimed in claim 1, wherein the stimulatory information is a group of patterns, comprising optical patterns, acoustic patterns, or a combination thereof.

5. The control system as claimed in claim 1, wherein the biometric reaction of the user is measured by electroencephalogram, electrooculogram or electromyogram.

6. The control system as claimed in claim 5, wherein, by means of an EEC reading (electroencephalogram reading), it can be deteimined whether terms, scenes or other things are known to the user.

7. A method for access control of an application system, comprising:
   presenting stimulatory information to a user, wherein the presentation of the stimulatory information triggers a biometric reaction comprising a brain pattern of the user, wherein the stimulatory information is presented exclusively to the user who is to be authorized for an application system, and wherein no user information is assigned to the stimulatory information;
   acquiring via an acquisition device current data comprising electrically measurable data of the user as a result of the biometric reaction;
   assigning a unique authorization to the stimulatory information;
   triggering the biometric reaction of the user by a recollection of the presented stimulatory information;
   comparing the acquired current data to provide a comparison result, wherein from a mental reaction of the user it is determined whether the user has recognized the stimulatory information; and
   authorizing the user directly for the application system if the stimulatory information is known to the user.

8. The method as claimed in claim 7, wherein the stimulatory information is provided as a group of patterns, comprising optical patterns, acoustic patterns, or a combination thereof.

9. The method as claimed in claim 7, wherein the biometric reaction of the user is measured via an electroencephalogram, an electrooculogram or an electromyogram.

10. The method as claimed in claim 9, wherein, by means of an EEC reading (electroencephalogram reading), it can be determined whether terms, scenes or other things are known to the user.

* * * * *